US009581579B2

(12) United States Patent
Lin et al.

(10) Patent No.: US 9,581,579 B2
(45) Date of Patent: Feb. 28, 2017

(54) QUICK EXTRACTION KIT ADAPTED TO A PROCEDURE OF DETECTING PESTICIDE RESIDUES IN AGRICULTURAL PRODUCTS AND A METHOD OF OBTAINING A PRIMARY TEST LIQUID FROM AN AGRICULTURAL SAMPLE BY THE QUICK EXTRACTION KIT

(71) Applicant: AGRICULTURAL CHEMICALS AND TOXIC SUBSTANCES RESEARCH INSTITUTE, COUNCIL OF AGRICULTURE, Taichung (TW)

(72) Inventors: Shao-Kai Lin, Taichung (TW); Wei-Chen Chuang, Taichung (TW); Jou-Wen Chen, Taichung (TW)

(73) Assignee: AGRICULTURAL CHEMICALS AND TOXIC SUBSTANCES RESEARCH INSTITUTE, COUNCIL OF AGRICULTURE, EXECUTIVE YUAN, Taichung (TW)

( * ) Notice: Subject to any disclaimer, the term of this patent is extended or adjusted under 35 U.S.C. 154(b) by 0 days.

(21) Appl. No.: 14/469,202

(22) Filed: Aug. 26, 2014

(65) Prior Publication Data

US 2016/0018305 A1    Jan. 21, 2016

(30) Foreign Application Priority Data

Jul. 18, 2014    (TW) .............. 103124848 A

(51) Int. Cl.
*B01L 9/00* (2006.01)
*B01L 3/00* (2006.01)
(Continued)

(52) U.S. Cl.
CPC .............. *G01N 33/24* (2013.01); *G01N 1/405* (2013.01); *G01N 2033/245* (2013.01)

(58) Field of Classification Search
CPC ... Y10T 436/10; Y10T 436/00; G01N 1/4055; G01N 1/40; G01N 1/00; G01N 1/28; G01N 2001/4061; G01N 33/24; G01N 33/00; G01N 2033/245; G01N 2033/24; G01N 2033/00; G01N 1/4061
(Continued)

(56) References Cited

U.S. PATENT DOCUMENTS 6,541,273 B1    4/2003    Plaisance
7,666,686 B2 *  2/2010    Shelly, Jr. .............. B01J 20/103
                                                        436/177
(Continued)

FOREIGN PATENT DOCUMENTS

CN    202631493 U    12/2012
CN    103055540 A     4/2013
CN    103111091 A     5/2013

OTHER PUBLICATIONS

Restek, QuEChERS Methodology: Original Unbuffered Method Q-sep™ Packets—cat.# 23991 and 23992, Apr. 2012, pp. 1-4, obtained on Sep. 3, 2015.*

(Continued)

*Primary Examiner* — Christine T Mui
(74) *Attorney, Agent, or Firm* — Muncy, Geissler, Olds & Lowe, P.C.

(57) ABSTRACT

The present invention provides a quick extraction kit adapted to a procedure of detecting pesticide residues in agricultural products and a method of obtaining a primary test liquid from an agricultural sample by the quick extraction kit. The quick extraction kit comprises a pipe, a first powder mixture layer and a second powder mixture layer. The method of taking primary test liquid is performed as follows. First, obtaining fragments of the agricultural sample. Second, adding an extraction solvent into the fragments of the agricultural sample to obtain a sample solution.

(Continued)

Third, adding the sample solution into the pipe. Finally, driving the sample solution to export from the pipe to become the primary test liquid. The quick extraction kit and the method solve the problem of being unable to quickly obtain the result of detecting pesticide residues.

17 Claims, 2 Drawing Sheets

(51) Int. Cl.
  *G01N 33/24* (2006.01)
  *G01N 1/40* (2006.01)
(58) Field of Classification Search
  USPC .................................. 436/17; 422/430, 50
  See application file for complete search history.

(56) References Cited

U.S. PATENT DOCUMENTS

| | | | |
|---|---|---|---|
| 2007/0117222 A1* | 5/2007 | Sibanda | G01N 30/14 436/518 |
| 2009/0214734 A1* | 8/2009 | Kitayama | A23L 1/0156 426/424 |
| 2010/0105076 A1* | 4/2010 | Perollier | B01J 20/26 435/7.4 |

OTHER PUBLICATIONS

Shia, Jeremy C. et al, Multi-Residue Analysis of Pesticides in Fruit Using Disque, a Dispersive Solid Phase Extraction Kit, Aug. 2008, Waters, The Science of What's Possible, pp. 1-3.*

* cited by examiner

QUICK EXTRACTION KIT ADAPTED TO A PROCEDURE OF DETECTING PESTICIDE RESIDUES IN AGRICULTURAL PRODUCTS AND A METHOD OF OBTAINING A PRIMARY TEST LIQUID FROM AN AGRICULTURAL SAMPLE BY THE QUICK EXTRACTION KIT

BACKGROUND OF THE INVENTION (1) Field of the Invention

The present invention relates to a quick extraction kit and a method utilizing the quick extraction kit, and more particularly relates to a quick extraction kit adapted to a procedure of detecting pesticide residues in agricultural products and a method utilizing the quick extraction kit.

(2) Description of the Prior Art

It has been widespread to apply pesticides on crops for discouraging the pests to increase agricultural production. Based on food safety requirements, all countries in the world have set standards for pesticide residue testing to establish Maximum Residue Limits (MRL).

For determination of pesticide residues in fruits, vegetables, grains, dried beans, tea, spice and other herbaceous plants, an existing detection method is sampling, and then pre-treating the sample by the QuEChERS method (Quick, Easy, Cheap, Effective, Rugged, Safe) to get a primary test liquid which is dewatered and purified. Next, the primary test liquid is processed to form a test liquid suitable for being detected in instruments. The test liquid is detected by liquid chromatograph/tandem mass spectrometer or gas chromatograph/tandem mass spectrometer, and finally, data of the detected result of said instruments is processed to obtain a result of pesticide residues detection.

It takes much time for sample pretreatment by the method above. The QuEChERS method needs to carry out following steps:

Granulating the sample by a blender to obtain a homogenized sample for increasing contact area of the sample;

Weighing proper quantity of the sample, such as 10 gram;

Adding an extraction solvent, such as acetonitrile solution, into the homogenized sample, then strongly shaking the homogenized sample with the extraction solvent for a period of time to form an extraction liquid, the ratio of the homogenized sample and the extraction solvent is 1:1 in weight and volume, for example, each 10 gram sample need to be added 10 ml acetonitrile solution;

Adding proper quantity of a mixture buffer agent, such as 6.5 gram, into the extraction liquid, wherein the mixture buffer agent has components comprising 4 gram anhydrous magnesium sulfate, 1 gram sodium chloride, 1 gram trisodium citrate and 0.5 gram disodium hydrogen citrate;

Strongly shaking the extraction liquid added the mixture buffer agent for a period of time by a homogenizer (SPEX SamplePrep 2010 GenoGrinder®), then centrifuging the extraction liquid added the mixture buffer agent to make the extraction liquid stratified by a centrifuge;

Taking proper quantity of a supernatant of the extraction liquid, such as 6 ml; and Based on the type of the sample, adding different adsorbents into the supernatant.

For example, when the sample is fruit, vegetable or crop, the adsorbent is a mixture of 150 mg primary secondary amine (PSA) and 900 mg anhydrous magnesium sulfate; if the sample is tea, the adsorbent is a mixture of 450 mg PSA and 900 mg anhydrous magnesium sulfate; if the sample comprises carotenoid, the adsorbent is a mixture of 150 mg PSA, 855 mg anhydrous magnesium sulfate and 15 mg graphitized carbon black (GCB). Besides, if the sample contains high quantity of chlorophyll, the adsorbent is a mixture of 150 mg PSA, 855 mg anhydrous magnesium sulfate and 45 mg GCB.

Afterward, the supernatant added the adsorbent is strongly shaken for a period of time by the homogenizer and then centrifuged by the centrifuge to obtain a centrifugal liquid for a primary test liquid.

The primary test liquid still should be treated by some steps to become the test liquid which is capable of being detected by instruments. For example, the primary test liquid is separately treated by a step of air drying, a step of adding methanol, acetone or hexane, a step of adding formic acid and a step of filtering by a filter membrane in sequence.

It takes about two hours to obtain the required primary test liquid from the sample by the QuEChERS method which would slow down the speed of the procedure of detecting pesticide residues and be impossible to quickly take the result of detecting pesticide residues. In view of this, it is important to provide an easier and faster method to obtain the required primary test liquid from the sample and solve said problem.

A solid phase extraction column to obtain a primary test liquid from a sample has been disclosed in the patent of CN103111091. However, the sample should be treated in the processes of shaking, twice-centrifuging, water-bathing and rotary evaporating to obtain a concentrated solution. The solid phase extraction column also needs to be treated by adding anhydrous sodium sulfate first and washing with acetonitrile/methyl benzene. Then, the concentrated solution is added into the treated solid phase extraction column to obtain the primary test liquid. Although the solid phase extraction column of said patent is filled in two layers of different materials (the upper layer consists of amino Silica NH2 and amide-modified polyethylene divinylbenzene, the bottom layer consists of graphite carbon), it still need much time for treating the sample and the solid phase extraction column to obtain the primary test liquid from the sample by the solid phase extraction column.

A solid phase extraction column has been disclosed in the patent of CN202631493, the solid phase extraction column is filled by three layers which are PSA, HBL and GCB. Because of these three layers all are absorbents, if the solid phase extraction column is used in the QuEChERS method mentioned above, the sample still needs the treatments of adding the mixture buffer agent, shaking and centrifuging after adding the extraction solvent. The primary test liquid then is obtained from the sample by the solid phase extraction column.

A similar technique has been disclosed in the patent of CN103055540. This patent has disclosed a purified column which is filled by a monolayer adsorbing filter. The adsorbing filter is a filter mixture of N-propyl ethylenediamine and anhydrous magnesium sulfate, a filter mixture of multi-walled carbon nanotubes and anhydrous magnesium sulfate, or a filter mixture of PSA, anhydrous magnesium sulfate, multi-walled carbon nanotubes and GCB. These filter mixtures are used for absorbents. Like the patent of CN202631493, even utilizing the purified column in the QuEChERS method, it also takes much time to obtain the primary test liquid for the sample treated by adding a mixture buffer agent, shaking and centrifuging.

Besides, the patent of U.S. Pat. No. 6,541,273 has disclosed a solid phase extraction cartridge filled in multi-layer absorbents, but it still spends much time to centrifuge a sample before obtaining a primary test liquid.

From the above description, obviously, it is impossible to quickly obtain the result of detection by the QuEChERS method, which spends too much time to obtain the primary test liquid. However, this problem is obviously unable to be solved by the solid phase extraction column of the prior art.

SUMMARY OF THE INVENTION

To solve the aforementioned problems, an exemplary embodiment of the invention provides a quick extraction kit and a method of obtaining a primary test liquid from an agricultural sample by the quick extraction kit, which are able to significantly enhance the speed of the procedure of detecting pesticide residues.

The quick extraction kit is adapted to a procedure of detecting pesticide residues in agricultural products, and the quick extraction kit comprises a pipe, a first powder mixture layer and a second powder mixture layer. The pipe has an output port located at the bottom of the pipe and an input port located at the top of the pipe, the output port is adapted to be input a sample solution, and the sample solution is a mixture solution obtained by treatment of shaking homogenized fragments of an agricultural sample with an extraction solvent.

The first powder mixture layer is in a form of powder and filled in the pipe, the first powder mixture layer is capable of absorbing the most water of the sample solution and buffering pH value of the sample solution when the sample solution flows through the first powder mixture layer. The second powder mixture layer is in a form of powder, filled in the pipe and between the first powder mixture layer and the output port, the second powder mixture layer is capable of absorbing the rest water of the sample solution and absorbing impurities interfering with detection of the sample solution.

The method for obtaining a primary test liquid from an agricultural sample comprise the following steps: homogenizing the agricultural sample to get fragments of the agricultural sample; shaking the homogenized fragments of the agricultural sample with an extraction solvent to obtain a sample solution, wherein each 1±0.03 g fragments of the agricultural sample are need to be added into 1 to 10 mL extraction solution; adding the sample solution into said pipe of quick extraction kit of claim 1; and driving the sample solution in the pipe to flow through the first powder mixture layer and the second powder mixture layer in sequence to export the primary test liquid from the output port of the pipe.

It is to be understood that both the foregoing general description and the following detailed description are exemplary and intended to provide further explanation of the invention as claimed. In order to make the features and the advantages of the invention comprehensible, exemplary embodiments accompanied with figures are described in detail below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figures 1, 2:
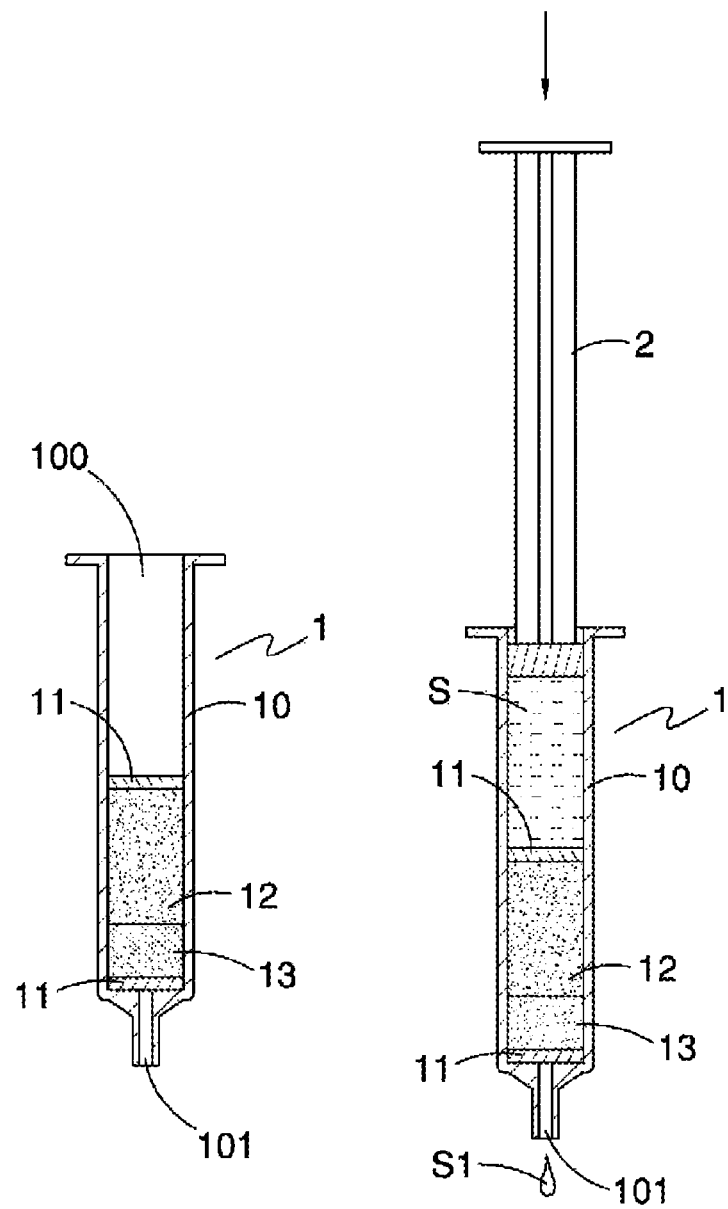
FIG. 1 is a schematic diagram of a quick extraction kit according to a preferred embodiment of the present invention.
FIG. 2 is another schematic diagram of a quick extraction kit according to a preferred embodiment of the present invention.

FIG. 1 is a preferred embodiment of this invention, a quick extraction kit 1 comprises a pipe 10, a first powder mixture layer 12 filled in the pipe 10 and a second powder mixture layer 13 filled in the pipe 10. The pipe 10 is preferably a cylindrical pipe. The pipe 10 has an output port 101 located at the bottom of the pipe 10 and an input port 100 located at the top of the pipe 10. The first powder mixture layer 12 is located below the bottom of the input port 100. The second powder mixture layer 13 is located below the first powder mixture layer 12 and above the output port 101. Besides, this invention further comprises two filter pads 11, one of the filter pads 11 is fixed on the top surface of the first powder mixture layer 12, and the other filter pad 11 is fixed on the bottom surface of the second powder mixture layer 13. The top surface of the second powder mixture layer 13 may directly contact with the first powder mixture layer 12. Alternatively, a filter pad is inserted between the first powder mixture layer 12 and the second powder mixture layer 13 (not shown in FIG. 1).

The quick extraction kit 1 mentioned above is used in a procedure of detecting pesticide residues in agricultural products. This procedure comprises the method of taking a primary test liquid from an agricultural sample by the quick extraction kit, the method comprises the following steps.

Step a: homogenizing the agricultural sample by a homogenizer so as to treat the agricultural sample to form fragments of the agricultural sample.

The agricultural sample is taken from vegetables, fruits, crops, dried beans, tea leaves, spice and other herbaceous plants, for the detecting sample of pesticide residues detection.

Step b: adding an extraction solvent into the fragments of the agricultural sample and shaking strongly to obtain a sample solution S.

Each 1±0.03 gram fragments of the agricultural sample needs to add 1 to 10 mL extraction solvent. The extraction solvent is selected from acetonitrile solution or acetonitrile solution containing acid. Each 1±0.03 gram fragments of the agricultural sample is preferably added said 5 mL extraction solvent. The extraction solvent is preferably selected from acetonitrile solution containing 1% acetic acid.

Step c: adding the sample solution S into the pipe 10 of the quick extraction kit 1, shown as FIG. 2.

Step d: driving the sample solution S in the pipe to flow through the first powder mixture layer and the second powder mixture layer in sequence so as to export the primary test liquid from the output port of the pipe.

One of the preferred ways for driving the sample solution S to flow through the pipe is directly pressing the sample solution S by a piston rod 2 to drive the sample solution S in the pipe 10 to flow through the first powder mixture layer 12 and the second powder mixture layer 13 in sequence. In addition, the air exhausting method also can be used to drive the sample solution S in the pipe 10 to flow through the first powder mixture layer 12 and the second powder mixture layer 13 in sequence. In the air exhausting method, which using a suction device, containing a vacuum pump (not shown in figures) to connect the output port 101 of the pipe 10, is for sucking the sample solution S in the pipe 10 to flow out of the output port 101. A flow rate of the sample solution S is limited in a range of 0.01 to 0.2 mL/sec, preferably 0.05 ml/sec. The filter pad mentioned above should be a filter pad without affecting the flow rate.

The powder mixture of the first powder mixture layer 12 is able to absorb most of water of the sample solution S and buffer the pH value of the sample solution S. Therefore, most of water of the sample solution S is remained in the first powder mixture layer 12 after the sample solution S flows through the first powder mixture layer 12 and the pH value is kept in a range about 4 to 8 so that the sample solution S would not have an extreme pH value. Second, the second powder mixture layer 13 is able to absorb the rest water of the sample solution and impurities, such as organic acid or pigment, which interferes with the detected result of instruments when the sample solution S flows through the second powder mixture layer 13. Therefore, after the sample solution S flows through the second powder mixture layer 13, the sample solution S becomes a primary test liquid S1 without impurities or with few impurities. The primary test liquid S1 is collected in a tube 3.

The primary test liquid S1 can be directly detected by LC/MS-MS or GC/MS-MS to ensure whether the pesticide residues of the sample comply with a requirement. Alternatively, the primary test liquid S1 may firstly be treated by a step of air-drying the primary test liquid S1 and then the primary test liquid S1 only remains a little water, a step of adding methanol, acetone or hexane, a step of adding formic acid and a step of filtering by a filter membrane in sequence, and then detected by LC/MS-MS or GC/MS-MS.

Preferably, total volume of the powder agent for the first powder mixture layer 12 is 0.87 $cm^3$, and total weigh of the first powder mixture layer 12 is 2 gram. The pipe 10 has an inner diameter degrees selected on demand, and so the first powder mixture layer 12 has not been pressed tightly and is loose or fluffy during a process of being filled in the pipe 10 with selected inner diameter degrees. Area of the first powder mixture layer 12 in the pipe 10 is about 1.13 $cm^2$, and height of the first powder mixture layer 12 is about 2.05 cm. Namely, total volume of the first powder mixture layer 12 is about 2.317 $cm^3$, and density of the first powder mixture layer 12 is about 0.863 $g/cm^3$. A porosity of the first powder mixture layer 12 is about 50%~62%, so that the sample solution S flowing through the first powder mixture layer 12 would not has the problem of blockade or flowing too fast.

Therefore, the flow rate of the sample solution S flowing through the first powder mixture layer 12 can be controlled in an expected range. It makes most of water of the sample solution S able to be removed in the first powder mixture layer 12.

The description above is one preferred embodiment and not limits this invention. A weight of the first powder mixture layer 12 is preferably 0.4 to 5 gram. A density of the first powder mixture layer 12 filled in the pipe 10 is preferably 0.7 to 1.3 $g/cm^3$. In view of volume, an area of the first powder mixture layer 12 filled in the pipe 10 is preferably 0.6 to 7.1 $cm^2$. A height of the first powder mixture layer 12 filled in the pipe 10 is preferably 1 to 8 cm. Besides, in view of porosity, a total porosity of the first powder mixture layer 12 filled in the pipe 10 is preferably 35~70%.

The above total porosity equates (the total volume of the first powder mixture layer 12 filled in the pipe 10–the real volume of the first powder mixture layer 12)/(the total volume of the first powder mixture layer 12 filled in the pipe 10)×100%.

In the present invention, a powder components of the first powder mixture layer 12 comprise anhydrous magnesium sulfate, sodium chloride, trisodium citrate and disodium hydrogen citrate. Furthermore, the first powder mixture layer 12 preferably consists of 1.23 gram anhydrous magnesium sulfate powder, 0.31 gram sodium chloride powder, 0.31 gram trisodium citrate powder and 0.15 gram disodium hydrogen citrate, but the invention is not limited to this. For example, 0.2 to 2 gram anhydrous magnesium sulfate powder, 0.1 to 1 gram sodium chloride powder, 0.1 to 1 gram trisodium citrate powder and 0.5 to 1 gram disodium hydrogen citrate are preferred consist selection.

In this invention, a weight of the second powder mixture layer 13 is preferably 0.2 gram to 1.6 gram, and the weight of the second powder mixture layer 13 is preferably less than the weight of the first powder mixture layer 12. 0.2 to 1.6 gram is also a preferred weight of the second powder mixture layer 13. In view of volume, it is preferred that an area and a height of the second powder mixture layer 13 in the pipe 10 are 1.13 cm2 and 0.8 cm or an area and a height of the second powder mixture layer 13 in the pipe 10 are 0.6 to 7.1 $cm^2$ and 0.23~3 cm. Wherein the height of the second powder mixture layer 13 is lower than the height of the first powder mixture layer 12 in the pipe 10.

When the agricultural sample is selected from general vegetables and fruits, a powder component of the second powder mixture layer 12 comprises PSA (primary secondary amine) powder and anhydrous magnesium sulfate powder. Furthermore, the second powder mixture layer 13 consists of 0.1 gram PSA powder and 0.6 gram anhydrous magnesium sulfate powder but the invention is not limited to this example. 0.01 to 0.5 gram PSA powder and 0.2 to 1 gram anhydrous magnesium sulfate powder and 0.001 to 0.1 gram GCB powder are also preferred. The preferred ratio of weight of GCB powder and anhydrous magnesium sulfate powder is about 1/79. The anhydrous magnesium sulfate powder of the second powder mixture layer 13 is less than the anhydrous magnesium sulfate powder of the first powder mixture layer 12.

Figures 3, 4:
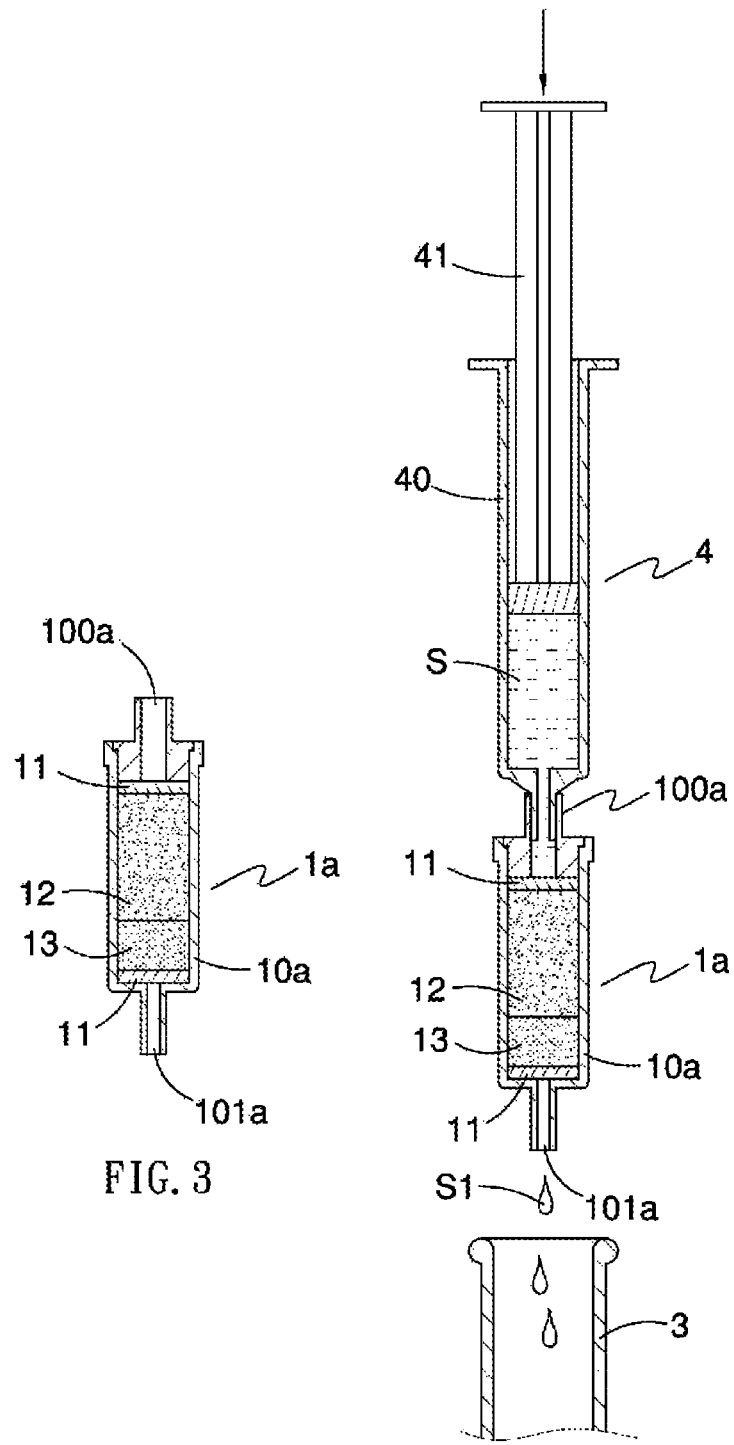
FIG. 3 is a schematic diagram of a quick extraction kit according to another preferred embodiment of the present invention.
FIG. 4 is another schematic diagram of a quick extraction kit according to another preferred embodiment of the present invention.

FIGS. 3 and 4 show another preferred embodiment of this invention, the pipe 10a of the quick extraction kit 1a in this embodiment is slightly different from the pipe 10 in form. The pipe 10a also comprises an input port 100a and an output port 101a. The pipe 10a is also packed with at least two filter pads 11, a first powder mixture layer 12 and a second powder mixture layer 13.

A difference there between is that the sample solution S is added in a tube 40 of an injection tube 4, and a bottom of the tube 40 connects with the input port 100a. When directly pressing the sample solution S by a piston rod 41 of the injection tube 4, the sample solution S is immediately injected into the pipe 10a to flow through the first powder mixture layer 12 and the second powder mixture layer 13 in sequence to become the primary test liquid S1 which is selected by the tube 3.

From the above description, the sample solution S consisted of the fragments of the sample and the extraction solution is able to be directly extracted by the quick extraction kit 1 or 1a to obtain the primary test liquid. Compared with the existing QuEChERS method, the process of obtaining the primary test liquid by the quick extraction kit 1 or 1a gets rid of one treatment of shaking and two treatments of centrifugation. Therefore, it significantly decreases the time of obtaining the primary test liquid from the sample by the quick extraction kit 1 or 1a. The speed of the procedure of detecting pesticide residues is also significantly enhanced by the quick extraction kit 1 or 1a so that the problem of being unable to quickly obtain the detection result in the prior art is solved.

Besides, in the existing QuEChERS method, each 1 gram homogenized sample needs to be added into 1 ml extraction solvent (Acetonitrile). In a preferred example of this invention, each 1 gram homogenized sample needs to be added into 5 ml extraction solvent. In other word, a dilution multiple of the QuEChERS method is 1, a dilution multiple of this invention is 5. Therefore, a content of an unit sample of the primary test liquid obtained by the method of this invention (about 0.2 g/mL) is lower than an unit sample of the primary test liquid obtained by the QuEChERS method. It means that an interfered level affected by substrate in the detection result of the primary test liquid obtained by the method of this invention significantly lower than that in the detection result of the primary test liquid obtained by the QuEChERS method when the primary test liquid is detected by instruments.

While the preferred embodiments of the present invention have been set forth for the purpose of disclosure, modifications of the disclosed embodiments of the present invention as well as other embodiments thereof may occur to those skilled in the art. Accordingly, the appended claims are intended to cover all embodiments which do not depart from the spirit and scope of the present invention.

What is claimed is:

1. A quick extraction kit for use in extracting pesticide residues from a homogenized sample with a solvent and subsequently cleaning those extracted pesticide residues for analysis, comprising:
    a pipe having an output port located at the bottom of the pipe and an input port located at the top of the pipe for receiving a sample solution obtained by shaking a mixture of the homogenized sample and the solvent;
    a first powder mixture layer filled in the pipe, being capable of absorbing most of water of the sample solution and buffering a pH value of the sample solution, but not pesticide residues contained in the sample solution, when the sample solution flows through the first powder mixture layer; and
    a second powder mixture layer filled in the pipe and between the first powder mixture layer and the output port, and being capable of absorbing the rest of water of the sample solution and impurities interfering with the analysis, but not the pesticide residues, when the sample solution flows through the second powder mixture layer so as to export from the output port a cleaned extract containing the pesticide residues ready for the analysis.

2. The quick extraction kit of claim 1, wherein a density of the first powder mixture layer in the pipe is 0.7 to 1.3 g/cm$^3$.

3. The quick extraction kit of claim 1, wherein a porosity of the first powder mixture layer in the pipe is 35 to 70%.

4. The quick extraction kit of claim 1, wherein the first powder mixture layer has components, comprising anhydrous magnesium sulfate powder for absorbing said most of water of the sample solution.

5. The quick extraction kit of claim 4, wherein the second powder mixture layer comprises anhydrous magnesium sulfate powder less than that in the first powder mixture layer, for absorbing the rest of water of the sample solution.

6. The quick extraction kit of claim 5, wherein the second powder mixture layer further comprises primary secondary amine powder, and graphitized carbon black powder for absorbing the impurities.

7. A method for extracting pesticide residues from an agricultural sample and subsequently cleaning those extracted pesticide residues for analysis, comprising:
    homogenizing the agricultural sample;
    shaking the homogenized agricultural sample with a solvent to obtain a sample solution;
    adding the sample solution into said pipe of the quick extraction kit of claim 1; and
    driving the sample solution in the pipe to flow through the first powder mixture layer and the second powder mixture layer in sequence to export from the output port of the pipe a cleaned extract containing the pesticide residues ready for the analysis.

8. The method of claim 7, wherein a flow rate of the sample solution is controlled in a range of about 0.01 to 0.2 mL/sec.

9. The method of claim 7, wherein the solvent comprises acetonitrile.

10. The method of claim 7, wherein a density of the first powder mixture layer in the pipe is 0.7 to 1.3 g/cm$^3$.

11. The method of claim 7, wherein a porosity of the first powder mixture layer in the pipe is 35 to 70%.

12. The method of claim 7, wherein the first powder mixture layer comprises anhydrous magnesium sulfate powder for absorbing said most of water of the sample solution.

13. The method of claim 12, wherein the second powder mixture layer comprises anhydrous magnesium sulfate powder less than that in the first powder mixture layer, for absorbing the rest of water of the sample solution.

14. The method of claim 13, wherein the second powder mixture layer further comprises primary secondary amine powder, and graphitized carbon black powder for absorbing the impurities.

15. The quick extraction kit of claim 1, further comprising:
    a first filter pad disposed above the first powder mixture layer for filtering out insoluble dregs from the sample solution; and
    a second filter pad disposed underneath the second powder mixture layer for filtering out insoluble dregs from the second power mixture layer.

16. The quick extraction kit of claim 1, further comprising a piston rod for driving the sample solution in the pipe to flow through the first powder mixture layer and the second powder mixture layer in sequence to discharge the cleaned extract.

17. The quick extraction kit of claim 1, further comprising an injection tube that includes a tube for receiving the sample solution, and a piston rod for driving the sample solution in the tube to flow through the first powder mixture layer and the second powder mixture layer in sequence to discharge the cleaned extract.

* * * * *